United States Patent
Boehm, Jr. et al.

(10) Patent No.: US 7,306,603 B2
(45) Date of Patent: Dec. 11, 2007

(54) DEVICE AND METHOD FOR PERCUTANEOUS PLACEMENT OF LUMBAR PEDICLE SCREWS AND CONNECTING RODS

(75) Inventors: Frank H. Boehm, Jr., Utica, NY (US); Benedetta D. Meinick, Rome, NY (US)

(73) Assignee: Innovative Spinal Technologies, Mansfield, MA (US)

( * ) Notice: Subject to any disclaimer, the term of this patent is extended or adjusted under 35 U.S.C. 154(b) by 231 days.

(21) Appl. No.: 10/320,989

(22) Filed: Dec. 17, 2002

(65) Prior Publication Data

US 2004/0039384 A1  Feb. 26, 2004

Related U.S. Application Data

(60) Provisional application No. 60/405,261, filed on Aug. 21, 2002.

(51) Int. Cl.
*A61B 17/56* (2006.01)
*A61F 2/30* (2006.01)

(52) U.S. Cl. ...................................................... 606/61

(58) Field of Classification Search .................. 606/53, 606/60, 61, 72, 73, 96; 600/425, 407; 403/331
See application file for complete search history.

(56) References Cited

U.S. PATENT DOCUMENTS

| | | | |
|---|---|---|---|
| 5,120,171 A * | 6/1992 | Lasner | 411/308 |
| 5,171,279 A * | 12/1992 | Mathews | 128/898 |
| 5,176,680 A | 1/1993 | Vignaud et al. | |
| 5,196,015 A * | 3/1993 | Neubardt | 606/61 |
| 5,526,812 A * | 6/1996 | Dumoulin et al. | 600/407 |
| 5,584,833 A | 12/1996 | Fournet-Fayard et al. | |
| 5,593,407 A | 1/1997 | Reis | |
| 5,628,740 A * | 5/1997 | Mullane | 606/61 |
| 5,643,260 A * | 7/1997 | Doherty | 606/61 |
| 5,649,947 A | 7/1997 | Auerbach et al. | |
| 5,716,355 A | 2/1998 | Jackson et al. | |
| 5,738,685 A | 4/1998 | Halm et al. | |
| 5,752,957 A | 5/1998 | Ralph et al. | |
| 5,910,142 A * | 6/1999 | Tatar | 606/61 |
| 6,033,406 A | 3/2000 | Mathews | |

(Continued)

FOREIGN PATENT DOCUMENTS

DE 94 02 695  4/1994

(Continued)

OTHER PUBLICATIONS

John W. Brantigan, M.D. et al., "Posterior Lumbar Interbody Fusion Technique Using the Variable Screw Placement Spinal Fixation System," SPINE, State of the Art Reviews, 1992.

(Continued)

*Primary Examiner*—Anuradha Ramana
(74) *Attorney, Agent, or Firm*—Carr LLP

(57) ABSTRACT

A minimally invasive method for stabilizing adjacent vertebrae to be fused is accomplished with a device configured to interlink the pedicles of the adjacent vertebrae and including multiple pedicle screws. Each of the pedicle screws has a screw head configured to receive a connecting rod in a position, in which the rod and the receiving pedicle screw are vertically aligned.

14 Claims, 11 Drawing Sheets

U.S. PATENT DOCUMENTS

| | | |
|---|---|---|
| 6,214,050 B1 | 4/2001 | Huene |
| 6,264,658 B1 * | 7/2001 | Lee et al. .................. 606/61 |
| 6,287,313 B1 | 9/2001 | Sasso |
| 6,342,056 B1 | 1/2002 | Mac-Thiong et al. |
| 6,443,953 B1 | 9/2002 | Perra et al. |
| 6,488,682 B2 | 12/2002 | Kikuchi et al. |
| 6,530,929 B1 | 3/2003 | Justis et al. |
| 6,546,277 B1 * | 4/2003 | Franck et al. ............. 600/426 |
| 6,660,006 B2 | 12/2003 | Markworth et al. |
| 6,743,231 B1 | 6/2004 | Gray et al. |
| 6,755,829 B1 * | 6/2004 | Bono et al. .................. 606/61 |
| 6,802,844 B2 * | 10/2004 | Ferree ........................ 606/61 |
| 6,932,822 B2 | 8/2005 | Oribe et al. |
| 7,008,422 B2 | 3/2006 | Foley et al. |
| 7,011,660 B2 | 3/2006 | Sherman et al. |
| 2002/0058942 A1 | 5/2002 | Biedermann et al. |
| 2002/0161368 A1 | 10/2002 | Foley et al. |
| 2003/0199872 A1 | 10/2003 | Markworth et al. |
| 2004/0049191 A1 | 3/2004 | Markworth et al. |
| 2004/0260287 A1 | 12/2004 | Ferree |
| 2005/0021031 A1 | 1/2005 | Foley et al. |
| 2005/0137593 A1 | 6/2005 | Gray et al. |
| 2005/0203530 A1 | 9/2005 | Oribe et al. |
| 2006/0111714 A1 | 5/2006 | Foley |
| 2006/0200135 A1 | 9/2006 | Sherman et al. |
| 2006/0229614 A1 | 10/2006 | Foley et al. |

FOREIGN PATENT DOCUMENTS

| | | |
|---|---|---|
| FR | 2 659 546 | 9/1991 |
| WO | WO 01/28436 | 4/2001 |
| WO | WO 2004/098466 | 11/2004 |

OTHER PUBLICATIONS

European Search Report 03793332.2-2318 dated Jun. 20, 2007.
New Zealand Examination Report 538853 dated Jun. 7, 2007.

* cited by examiner

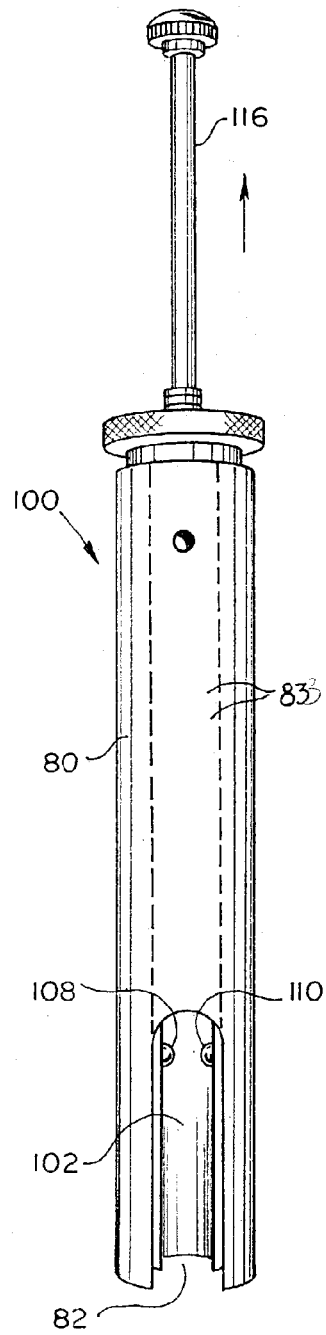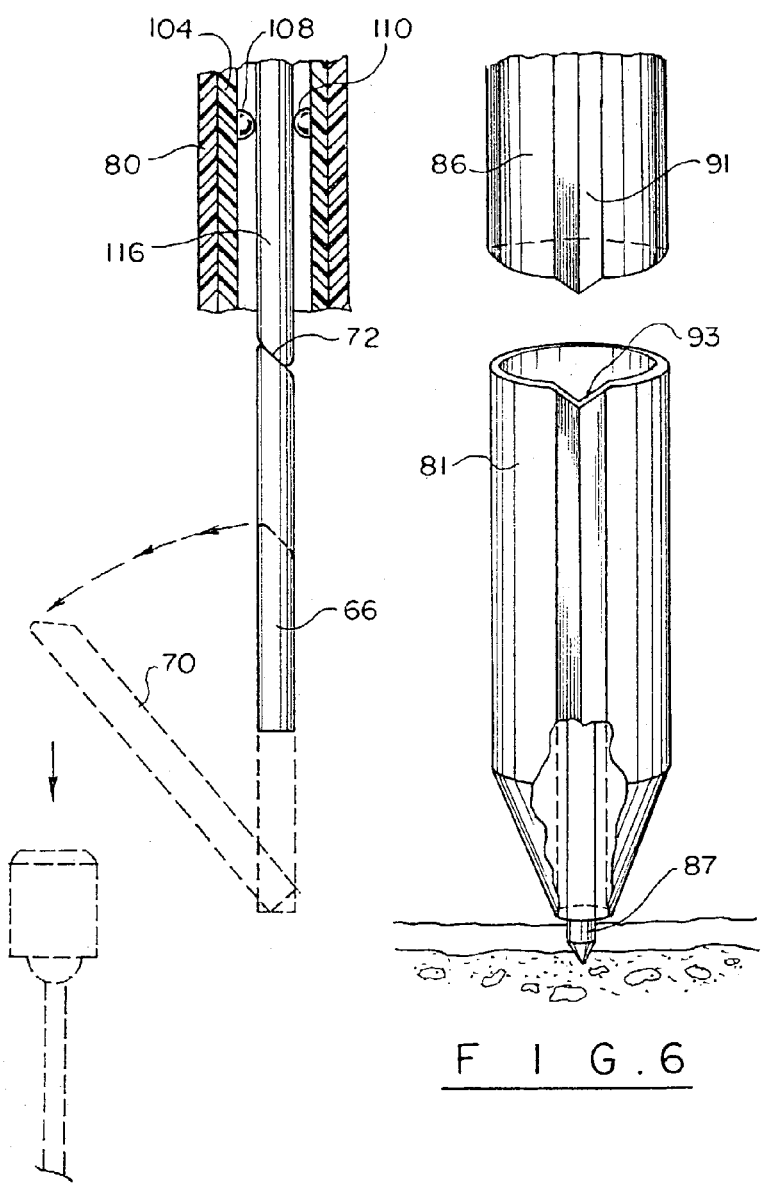
FIG. 8
FIG. 9
FIG. 6

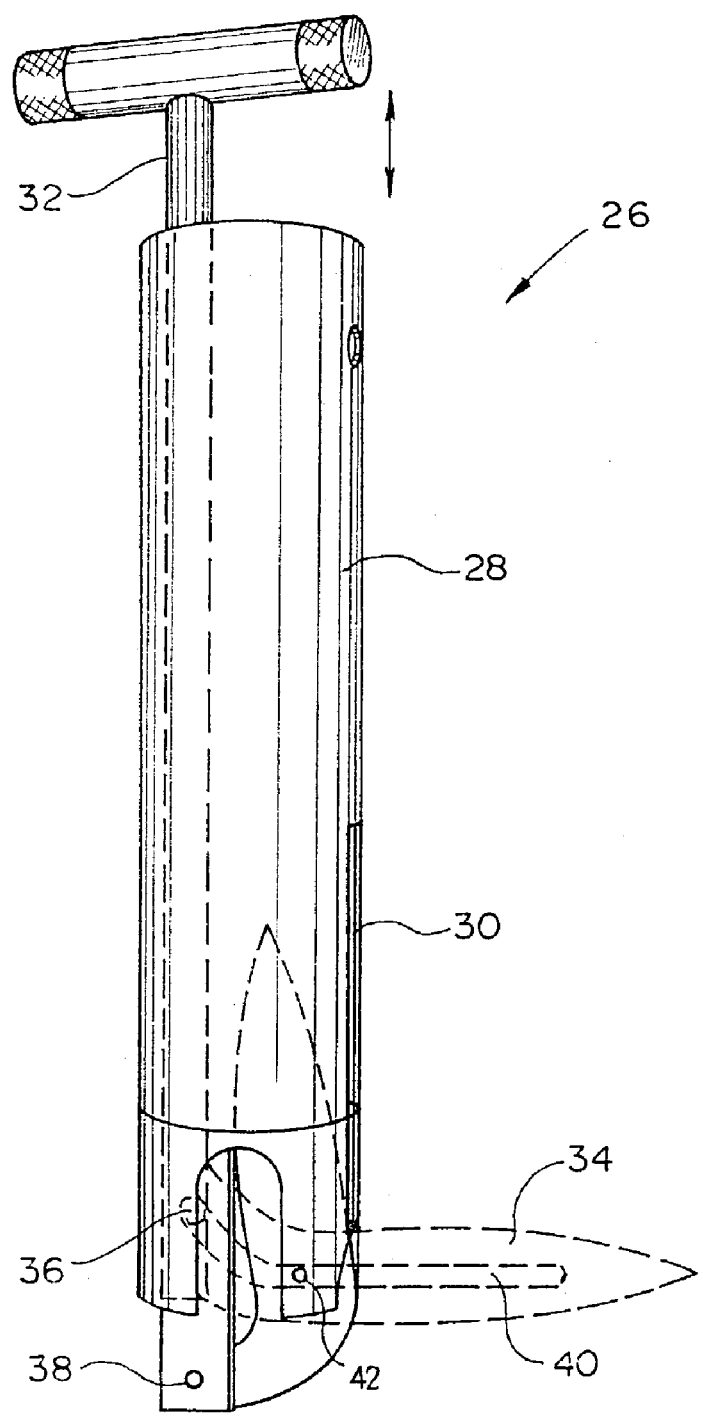
F I G . 7

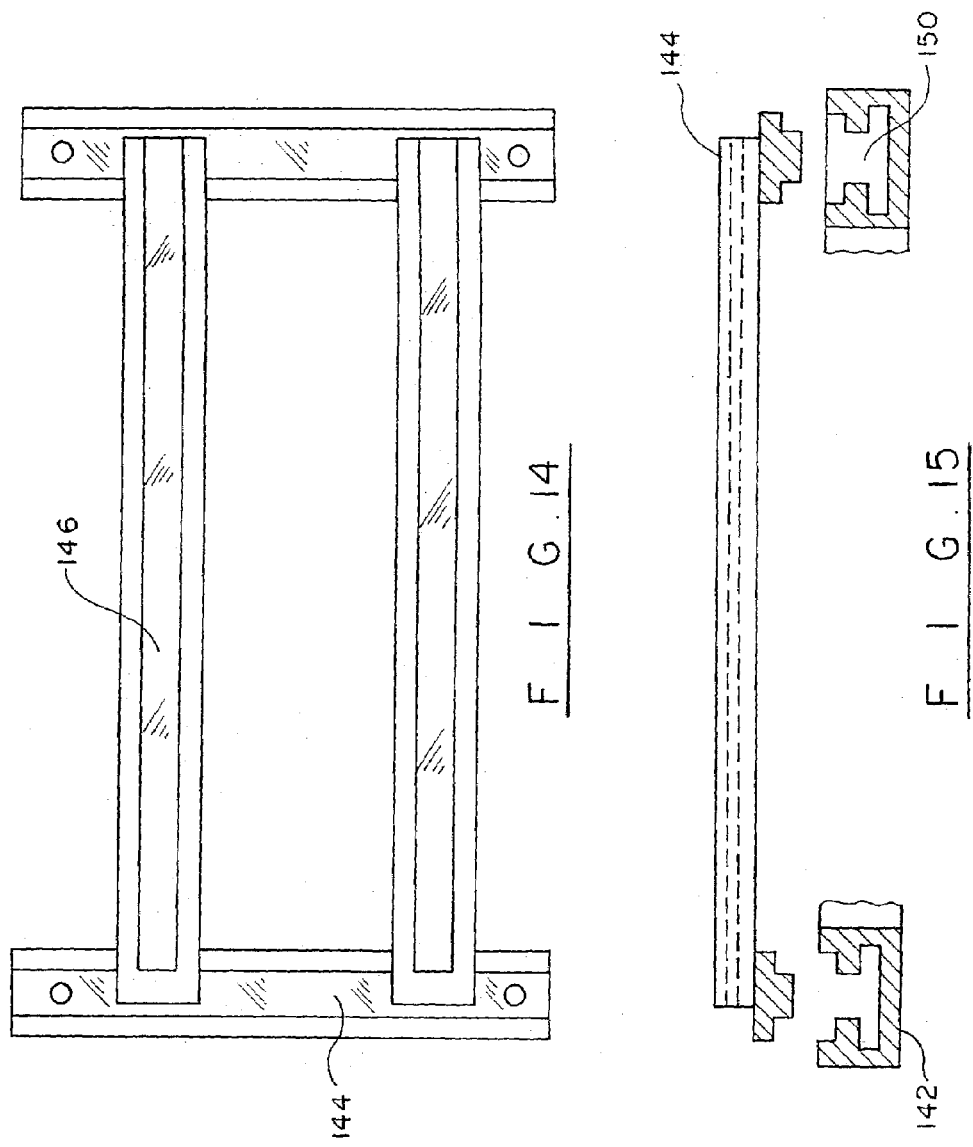

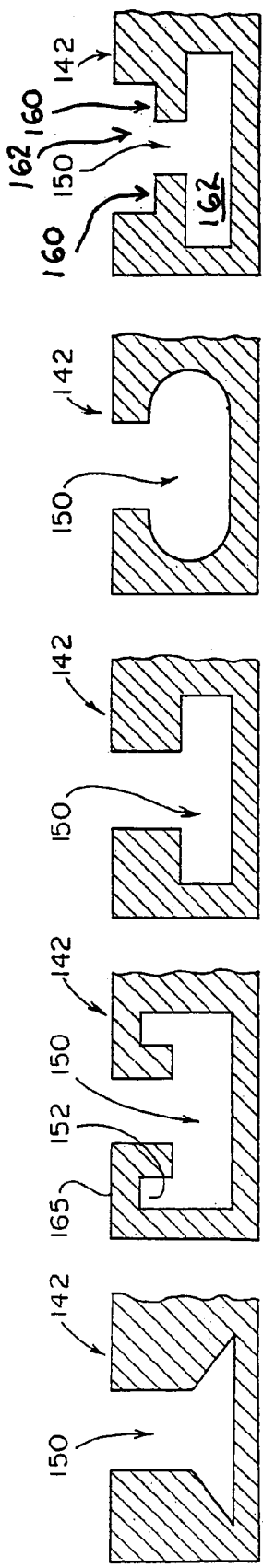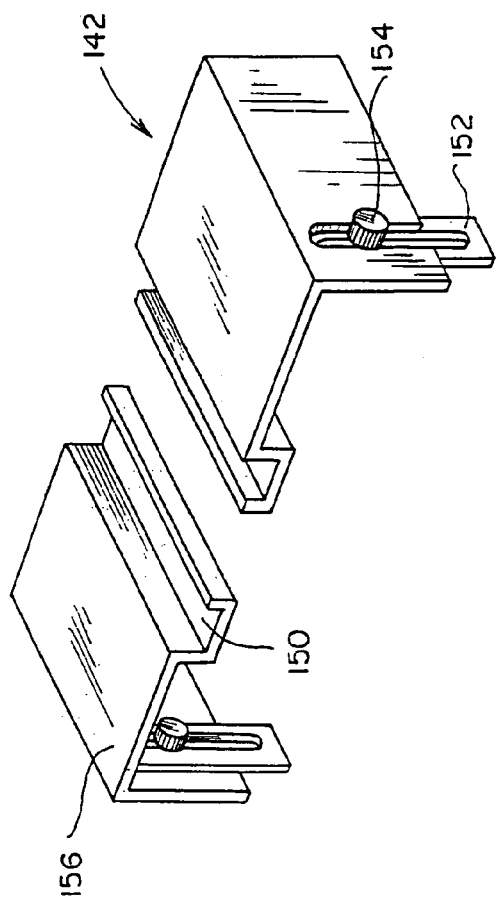

DEVICE AND METHOD FOR PERCUTANEOUS PLACEMENT OF LUMBAR PEDICLE SCREWS AND CONNECTING RODS

CROSS REFERENCE TO RELATED APPLICATION

This application is based on and claims priority to a U.S. Provisional Application No. 60/405,261 filed on Aug. 21, 2002 and fully incorporated herein by reference

BACKGROUND OF THE INVENTION

1. Field of the Invention

The present invention relates to an instrumentation system, and method for operating the same, used in fusion procedures of the spine. In particular, the invention relates to an instrumentation system for subcutaneously interlocking pedicles of adjacent vertebra to be fused and to a minimally-invasive posterior-approach method of interlocking the pedicles.

2. Background of the Related Prior Art

Over the past twenty years, the value of pedicle screw stabilization in enhancing fusion procedures of the lumbar spine has been proven unambiguously. Many systems have been introduced to achieve this, and presently, numerous systems exist for the placement of screws and connecting rod or plate systems as a component of a classic lumbar fusion procedure. Most of these systems require an "open," procedure, involving an extensive incision of the skin, extensive detachment or "takedown" of the paravertebral muscles, and exposure of the bony elements. This involves a significant, complex surgical intervention, with massive dissection of the paravertebral musculature. As a consequence, the classic lumbar fusion procedure is associated with significant morbidity, including blood loss, increased anesthesia time with its attendant complications, and increased risk of infection. Additionally, quite often the patient experiences significant postoperative pain requiring longer hospital stay which adds substantial cost to the current systems.

One of these procedures developed to overcome the drawbacks of the classic fusion procedure includes the use of unique endoscopic equipment. The cost of such equipment can be prohibitively high which limits the use of this procedure to a few medical facilities. Still another undesirable consequence of the endoscopic procedure is its complexity, requiring considerable experience of a medical staff capable of using this equipment to properly place the screws as well as a staff of highly trained technicians.

U.S. Pat. No. 6,443,953 discloses the other, more commonly performed procedure associated with a system which is configured to interlock the pedicles of the vertebral bodies to be fused and includes inserting multiple screws into pedicles and bridging the screw heads of the screws by a connecting rod. As illustrated in FIGS. 1 and 2, implementation of such a procedure requires that a superior positioned incision be made in the paravertebral tissues of the lower thoracic area located below the lowest of the screws 22. Connecting rod 14 is then passed parallel to the spine, as indicated by an arrow A, through holes 18 in the screw heads 12 and is secured into position by initially topping the screw heads 12 with caps 20 and, further, by placing nuts 16 in the caps 20. Displacement of the rod 14 through soft tissues, otherwise uninvolved by the procedure, introduces potential injury to these soft tissues. Furthermore, this procedure requires the precise alignment of the screws and, particularly, each of the holes 18 of the adjacent screw heads 12 with the connecting rod 14 as well as with one another. Hence, the procedure is associated with additional requirements imposed upon a surgeon, an increase in overall surgery time and, as a consequence, additional health risks for the patient.

Yet another problem associated with the above discussed system is the issue of passing bone screws into the pedicles of the lumbar spine in such a fashion that with merely the use of surface anatomy, in conjunction with intraoperative imaging, the screws can be secured into the pedicles with maximum purchase of bone and minimum risk of injury to peri-pedicular structures, such as nerve roots.

It is, therefore, desirable to provide an instrumentation system and a method for using the same that minimize the disturbance of soft tissue, reduce the overall time of surgery, optimize the guidance of the connecting rod toward screws and simplify the placement of the rod and the screws.

SUMMARY OF THE INVENTION

This objective is attained by the inventive system configured so that a connecting rod is initially introduced into one of the screws from above, not laterally, as taught by the prior art, and further, is operative to bridge adjacent screws.

One aspect of the invention relates to a new method of interlinking vertebra to be fused providing, initially, for pivotally coupling the leading end of the connecting rod to one of multiples screws inserted into the pedicles of the vertebra to be fused. To complete the interlinking of the vertebra, the inventive method further provides for pivoting the connecting rod about its leading end so that the trailing end of the rod engages an adjacent screw attached to the pedicle of the other one of the vertebra.

In contrast to the known prior art methods, in which the connecting rod is introduced below and above the screws and guided through soft tissues parallel to the spine, the inventive system allows the surgeon to guide the connecting rod towards one of the screws vertically. Therefore, one of the advantages of the inventive method is that penetration through soft tissues is localized, and, as a consequence, the cut soft tissues are only minimally disturbed.

A further aspect of the invention relates to a guide system for subcutaneously placing the screws in the pedicles to be interlinked. Configuration of the inventive guide system allows a surgeon to guide and position the screws so that coupling and displacement of the connecting rod between its primary and final positions is performed in a simple and reliable manner. Thus, a time-consuming and onerous alignment procedure, including displacement of the connecting rod through the holes of the screw heads, is significantly simplified. Accordingly, the safety of the inventive method is increased.

In accordance with another aspect of the invention, the inventive system provides for a rod holder system configured to cooperate with the guide system in a manner that ensures a pivotal coupling of the connecting rod with one of the screws. The rod holder system is further configured to direct displacement of the connecting rod to its final position, in which the screws are interlinked.

In accordance with still another aspect, the inventive system further includes an identification system configured to landmark the pedicles to be interlinked in a manner utilizing multiple imaging techniques. In accordance with still another aspect of the invention, the inventive system includes a placement system for directing and automatically placing the screw placing instruments in the desired position. The placement system is configured to allow a guide, providing the screws and screw placing instruments with the desired trajectory, to move in three mutually perpendicular planes relative to the landmarks. Accordingly, the operating surgeon is able to achieve high precision of positioning the guide relative to the identified entry points to the pedicles.

According to another aspect of the invention, there is an orthopedic/ neurosurgical kit including a combination of instruments, which are used during the performance of the inventive method. The kit providing the surgeon with a ready to be used assembly of guides, screws and screw placement instruments associated with the inventive method greatly facilitates the surgical procedure and, thus, reduces its cost.

It is, therefore, an object of the invention to provide a minimally-invasive surgical procedure for interlinking vertebra that avoids injury to tissues not otherwise involved in this procedure.

It is further an object of the invention to provide a placement system for positioning a variety of instruments associated with guiding and placing a pedicle screw and rod system of the inventive system.

It is another object of this invention to provide a system for the identification of the landmarks involved in placement of the screws-rod system.

It is yet another object of this invention to introduce a tissue cutting assembly cooperating with the guide system and configured to cut the soft tissue between the screw heads to create a tract receiving the connecting rod.

BRIEF DESCRIPTION OF THE DRAWINGS

The above and other objects, features and advantages will become more readily apparent from the detailed description of the preferred embodiment accompanied by the following drawings, in which:

FIG. 6 a front view of the guide system of the FIG. 5 illustrating a combination of an awl and outer and inner dilators;

FIG. 7 is an isometric view of a tissue cutting instrument configured in accordance with the invention;

FIG. 8 is an elevated front view of a rod holder system configured in accordance with the invention and shown in a primary position of the connecting rod in which the latter is engaged inside the rod holder;

FIG. 9 is a sectional view of the rod holder system of FIG. 7 illustrating the initial stage of the rod's displacement towards its final position;

FIG. 14 is a top view of a combination of the inner frame and the cradle frame of the placement system illustrated in FIG. 13;

FIG. 15 is a front view of the placement system illustrated in FIG. 13;

FIG. 16 is an embodiment of the outer frame of the positioning system shown in FIG. 13;

FIGS. 17–21 illustrate different embodiments of track structures provided in the outer frame of FIGS. 13 and 15 for engaging the inner frame of the placement system;

DETAILED DESCRIPTION OF THE PREFERRED EMBODIMENTS

Figure 1:
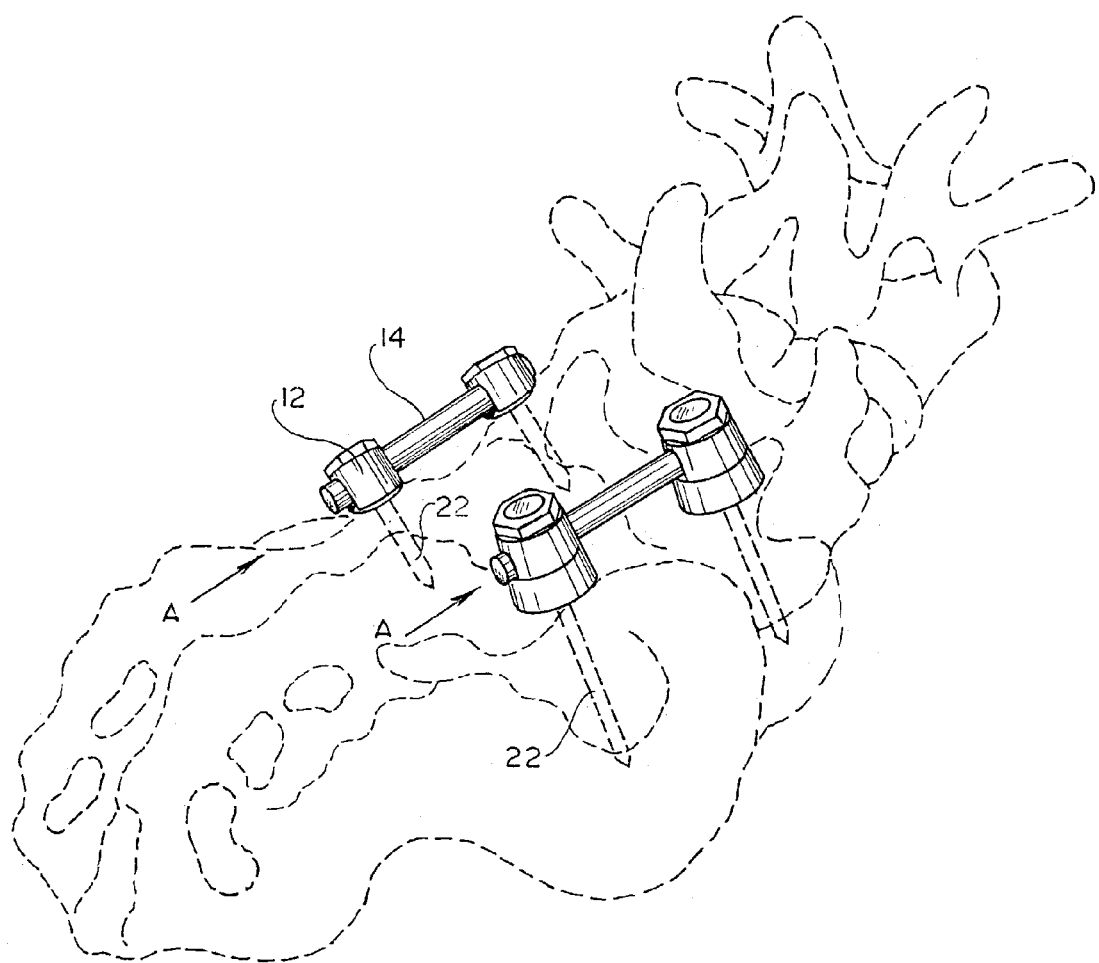
FIG. 1 is a side view of an instrumentation system of known prior art.
Figure 2:
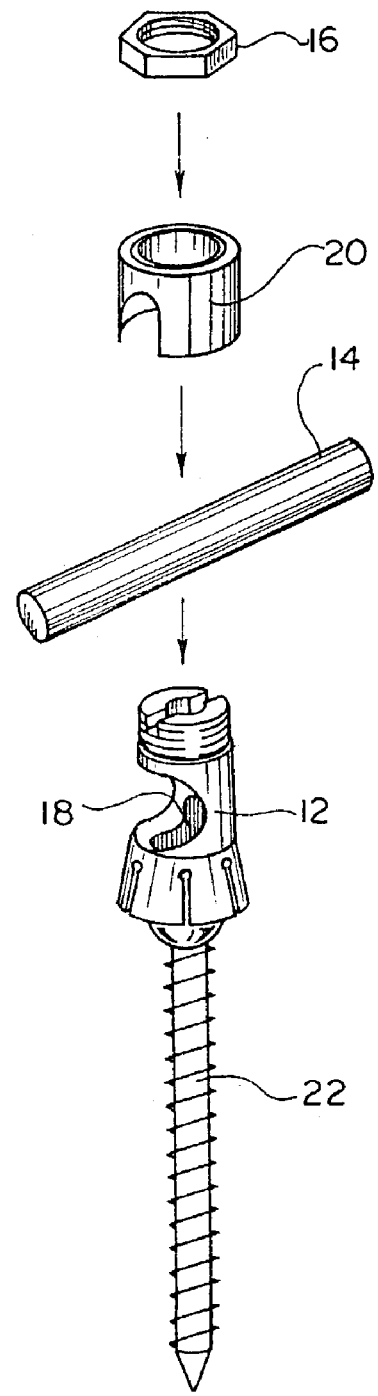
FIG. 2 is an exploded view of a screw of the instrumentation system illustrated in FIG. 1.
Figure 3:
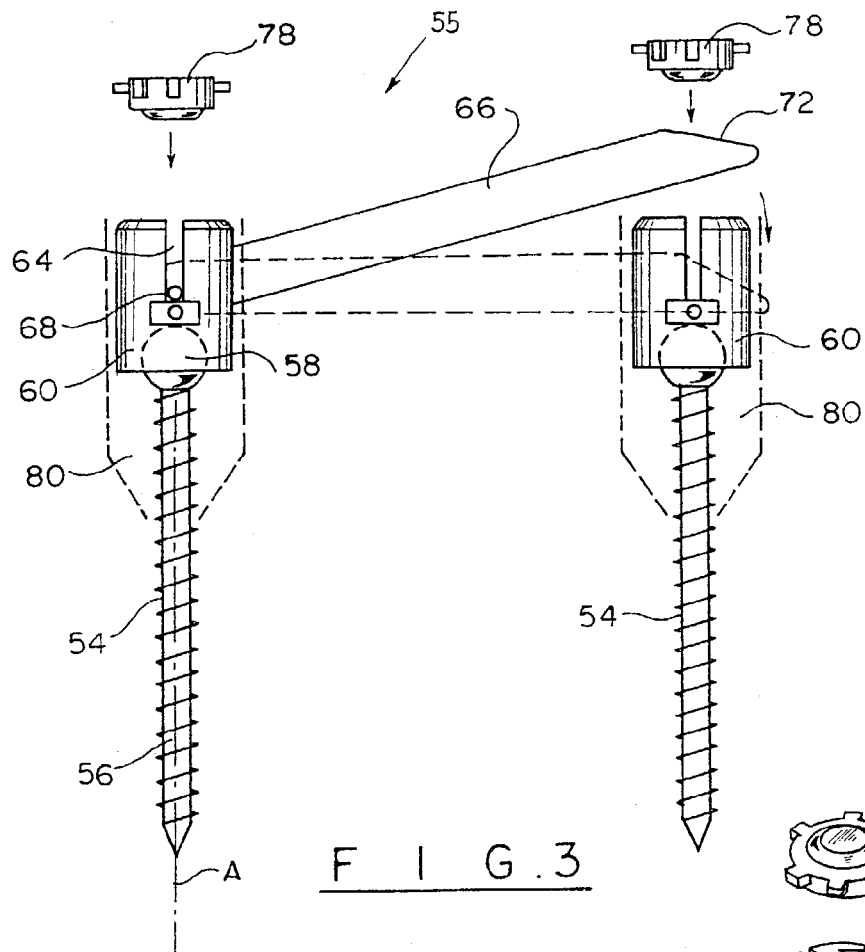
FIG. 3 is a side view of the inventive device.
Figure 4:
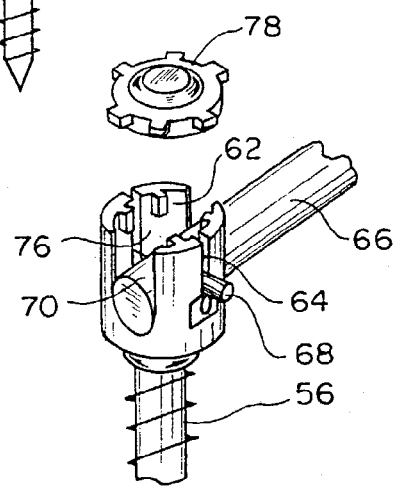
FIG. 4 is an isometric view of the inventive screw configured to be subcutaneously introduced into the pedicle of the vertebra.

As illustrated in FIGS. 3–4, the inventive method is performed to interlink vertebra to be fused by percutaneously guiding a connecting rod 66 in alignment with a longitudinal A-A axis of a screw 54 and, upon coupling the connecting rod 66 with this screw, pivoting the rod 66 so that it bridges adjacent screws 54. Accordingly, a pathway formed for one of the adjacent screws 54, which is advanced along this pathway towards the pedicle of one of the vertebra to be fused, is subsequently traversed by the connecting rod 66 that, thus, is automatically aligned with and engages a screw head 60 of the one screw 54.

Inventive system 55, configured to assist the surgeon to perform the inventive method, in addition to the screws 54 and the connecting rod 66, includes nuts 78 securing leading 70 (FIG. 4) and trailing 72 ends of the connecting rod 66 after the pedicle screws have been positioned relative to one another. Vertical displacement of the rod 66 requires that the screw head 60 be configured to receive the leading end 70 of the rod 66 from above in a first primary position of the rod 66, in which the latter and a shank 56 of the first screw 54 are aligned. Accordingly, the screw head 60 is formed with a peripheral wall defining a central opening dimensioned to receive the leading end 70 of the rod 66 in the primary position thereof. However, mere introduction of the leading end 70 of the rod 66 into the screw head 60 would be insufficient to prevent displacement of the rod 66 in the screw head 60 during pivotal motion of the rod 66 towards the adjacent screw 54. To reliably engage the leading end 70 of the rod 66 and the screw head 60 of the first screw 54, the peripheral wall of the screw head 60 is slotted and recessed. As shown in FIG. 4, two recesses 64, each formed in a respective segment of the peripheral wall, are aligned with one another and dimensioned to receive a pin 68 provided on the leading end 70 of the rod 66. The recesses 64 and the pin 68 are configured to provide rotational motion of the rod 66 about its leading end 70 while confining the latter within the screw head 60 between aligned slots 62 during the rotation of the rod 66. Thus, the screw head 60, receiving the leading end 70 of the rod 66 from above and having at least one slot 62 and a pair of recesses 64, which are dimensioned to allow the rod 66 to rotate, is critical to the successful performance of the inventive method.

Alternatively, the leading end 70 of the rod 66 can be permanently attached to the screw head 60. In accordance with this configuration of the screw 54, the pin 68 is formed as an integral part of the screw head 60, and the leading end 70 is permanently and pivotally mounted on the pin 68.

In its final position, as shown in phantom lines in FIG. 3, the trailing end 72 of the rod 66 engages the screw head 60 of the adjacent screw 54, which is inserted into the pedicle of the second one of the vertebra to be fused. As will be further explained, the trailing end 72 of the rod 66 is displaced along an arcuate path towards and placed through the slot 62 into the screw head 60 of the adjacent screw 54. To provide such an engagement between the rod 66 and the adjacent screw 54, the slots 62 formed in screw heads 60 of the one and adjacent screws 54 have to be located in a certain spatial relationship with respect to one another. In one spatial position, the slots 62 of the screw head 60 of the screw 54, receiving the trailing end 72 of the rod 66, and the screw 54 coupled to the leading end 70 can be aligned, if the rod 66 is straight. Alternatively, the slots 62 of the adjacent screws 54 can be located in a desired angular position relative to one another, if the rod 66 is curved. One of the reasons why the rod 66 may be curved is to connect the adjacent screws 54 introduced into the pedicles, which may extend at different angles, as is well known in the art. The curved rod is also useful in maintaining lordosis of the lumbar spine. To accommodate the curved rod, each of the screws 54 has a rotational component, such as a ratcheting or hinged mechanism, or a ball-in-socket joint 58, as shown in FIGS. 3 and 4. In the illustrated embodiment of the rotating component, the ball is preferably formed on the top of the shank 56. The screw head 60 of the screw 54 conjoins to the ball of the ball-in-socket joint 58 by the socket of the former, which surrounds the ball. In the shown configuration, the socket forms the undersurface or bottom of the screw head 60. This mechanism would allow the screw head 60 a substantial amount of rotational latitude, thus ultimately adjusting the path of the rod. Alternatively, the bottom of the head 60 may be provided with the ball, whereas the top of the shank 56 carries the socket.

Figure 5:
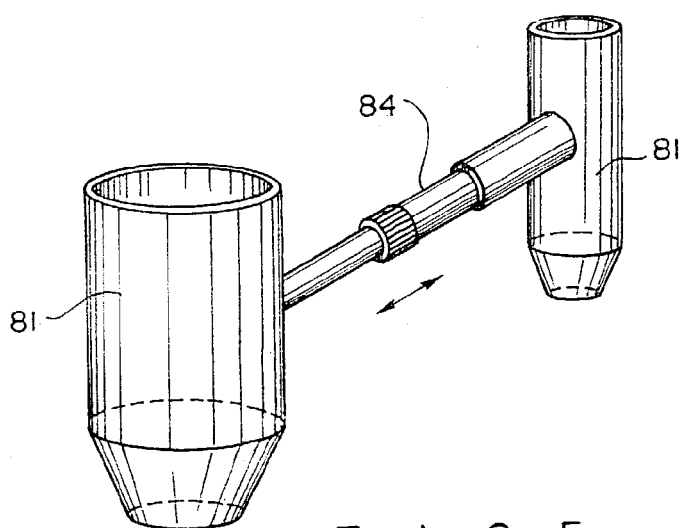
FIG. 5 is a view of one embodiment of a guide system configured to position multiple instruments associated with adjacent screws in a desired position.

FIGS. 5–6 illustrate a guide system configured to provide displacement of the screws 54 to the pedicles of the vertebra to be fused and to establish the desired position between the screw placement instruments associated with the adjacent screws 54. This system includes a pair of tubular sheaths 81 positioned in alignment with entry points of the screws 54 into the pedicles. The sheaths 81 may function as guides for further installation of screw placement instruments including a plurality of inner 86 and outer 80 dilators forming the pathways for the screws 54, which extend from the skin to the entry points of the screws into the pedicles to be interlinked.

This installation procedure may experience one problem. The adjacent screws 54 are to be interlinked by the connecting rod 66, which is displaced to its final position while the outer dilators 80 are still being locked in the pedicles for the reasons explained below. Accordingly, the rod 66 in the final position thereof should extend through the outer dilators 80, which, for this and other reasons, as explained below, are formed with slits 82. Therefore, the slits 82 are to be positioned so as to allow the rod 66 to penetrate through them before it interlinks the screws 54 in its final position. To provide such a desired position of the slits 82, the tubular sheaths 81 have to be placed relative to one another in a predetermined spatial relationship.

Changing the length of the retractable arm 84, having either a telescopic structure or a mechanism translating rotational motion into linear motion, allows the surgeon to properly place the sheaths 81 adjacent to the pedicles to be interlinked. After positioning of the sheaths 81, the screw placement instruments including inner 86 and outer dilators 80 are sequentially introduced over each of the sheaths 81 and lodged in the respective pedicles. The outer dilator 80 is provided with two to three small fixations pegs, so when it is positioned against the bone at the entry point to the pedicles, its position can be maintained through out the required portion of the surgery The retractable arm 84 allows the introduction of each subsequent dilator only in one position, in which the slits 82 of the progressively larger dilators straddle the opposite ends of the arm 84. Diameters of sequentially inserted and progressively larger dilators differ from one another such that each subsequent dilator has its inner diameter approximating the outer diameter of the previous dilator to prevent the entry of tissue into the plane between the two dilators while allowing relative displacement of the dilators 80, 86. Once the pathway, expanded by the subsequently introduced dilators, slightly exceeds the outer dimension of the screw head 60, the sheaths 81 and all inner dilators 86 are removed thus having the outer dilators 80 lodged against the pedicles so that their slits 82 are aligned.

Another configuration of the guide system includes the sheaths 81 and the retractable arms 84, which provides the initial desired position of the sheaths 81 relative to the pedicle. However, in this configuration, the retractable arm is removably attached to the sheaths 81 and is detached once the desired position of the sheath has been established. To maintain this desired position, which corresponds to the aligned position of the slits 82 of the outer dialators 80, the outer surfaces of the sheaths 81 have guiding surfaces 91. Mating with the guiding surfaces 91 are complementary shaped guiding surfaces 93 formed on the subsequently introduced inner and outer dilators 86,80. Accordingly, the outer dilators 80 lodged in the adjacent pedicles can be located relative to one another only in one position characterized by the aligned spatial relationship between the slits 82. The guiding surfaces 91, 93 can be formed along a part of the length of the sheaths and dilators and can be provided with various cross sections including rounded or polygonal projections and complementary shaped indents.

To ensure that the soft tissues would not penetrate between the subsequently installed inner 86 and outer 80 dilator, the dilators may be formed with displaceable panels 83 (see FIG. 8) uncovering the slit 82 after the dilators have been lodged in the pedicles. For the reasons explained below, except for the tip, the sheaths 81, dilators 80, 86, and awls 87 (FIG. 6) are preferably made from radiolucent material such as hard plastic, carbon fiber, or any other substance, which is firm to provide the pathway. The tips of the instruments, having contact with the pedicles, must be traced to prevent damage to the pedicles and, as a consequence, are made from radioopaque material depending on quality of which, the tips may be either reusable or disposable.

The dilators 80, 86 have respective tips configured to be relatively sharp to be able to penetrate percutaneously and to cut the subcutaneous tissue on their way towards the pedicles. The tip of the awl 87, which is designed to disrupt the pedicle for subsequent insertion of the screws 54, is much sharper than the tips of the dilators and can be formed with pyramidal, conical or rounded shape. It is advantageous, but not necessary, to initially install the awl 87 before the dilators. However, such a sequence helps avoid the possibility of injury with the sharp tip of the dilators in the event that placement is initially incorrect. It would also help maintain the sharpness of the starter awl if it were not exposed to the dense fibrous tissues, which must be dissected in order to create a passage from the skin to the entry point of the pedicle. The awls 87, guided either manually, or with the use of a standard operating room mallet, can be cannulated to allow for the passage of an orthopedic pin passable into pedicle to provide a guide for the screws 54 thus cannulated to be placed over the pin. Similarly to the dilators 80, 86, the tip of the awl 87 is made from radioopaque material to help the surgeon trace the awl's advancement during the surgery. The tip may be configured to be disposable for a single event so as to preserve its sharpness, or alternatively, it may be reusable.

Following the disruption of the cortex of the pedicles to be linked, the awls 87 are removed from the outer dilators 80 to allow for the passage of further instruments, that may, for example, be a drill, not shown in the drawings. As every other instrument guided through the outer dilator 80, the drill is configured such that the "wobble" thereof inside the outer dilator 80 is minimized. The pegs installed on the dilators are instrumental in reducing the wobble. One of the inventive configurations of the drill may include a guiding surface dimensioned and shaped to mate with the guiding surfaces 91 (FIG. 6) of the outer dilator 80. Furthermore, although the drill tip widens the initial disruption of the pedicle made by the awl 87, it still has a small diameter to prevent damage to the pedicle. Like the awl 87, the drill can be cannulated to provide a passage for a guide wire remaining in the tract upon removal of the drill, and the drill's tip is made from radioopaque material to trace the drill's position relative to the pedicle.

At this point, the screws 54 are introduced in a sequential manner into the adjacent pedicles of the vertebra to be fused located on one side of the spine and, then, when the entire procedure is repeated, another pair of the screws 54 is introduced into the pedicles located on the opposite side of the spine. The unique structure of the screws 54 allowing the rod 66 to be introduced vertically into the screw head 60 defines the ability of this system to achieve percutaneous placement of the screws and rods in accordance with the inventive method. Although the order of the placement of the screw is not important, it is desirable to introduce the screw 54 (FIG. 3) having the head 60 formed with the recesses 64 pivotally engaging the leading end 70 of the rod 66. The screws 54 penetrating the pedicle and vertebral body are preferably composed of titanium, although stainless steel, other metals, or any other material, including bioabsorbable materials could be utilized for performing the inventive method. Dimensions of the screws 54 are not limited to the uniform size, both in terms of the diameter of the screw as well as the length of the screw. The inner diameter of the screw may increase in size from the tip of the shank 56 of the screw 54 (FIG. 3) to the screw head 60 to maintain bone purchase while minimizing the risk of screw breakage. The tip, thread, and pitch of the screw are structured so as to allow the screws 54 to be passed into the pedicle and vertebral body without requiring complete drilling or tapping along the course and trajectory through the pedicle and vertebral body.

After the screws 54 have been subcutaneously placed in the pedicles, the surgeon would need to form a tract receiving the connecting rod 66 by percutaneously cutting the tissue between the subcutaneously placed screw heads 60. Referring to FIG. 7, a tissue-cutting instrument 26 has a cylindrical body 28 configured to slide through the outer dilator 80 in a manner similar to the other instruments. A blade 34 pivots between a rest position, in which the blade is withdrawn in the body 28, and a cutting position, when the blade extends through the slits 82 of the adjacent outer dilators 80. For safety reasons, in the rest position, the blade has to be fully withdrawn within the body 28, which is thus recessed at 30. Accordingly, displacement of the blade 34 is possible only when the recess 30 and the slit 82 of the outer dilator 80 are aligned. Such an aligned position can be automatically set by providing the opposing surfaces of the body 28 and the outer dilator 80 with the guiding surfaces 91 (FIG. 6) mating with one another to define the aligned position during displacement of the body 28 through the dilator 80.

A structure for pivoting the blade 34 includes a mechanism translating linear motion of a blade-actuating rod 32 into pivoting motion of the blade 34. As shown in FIG. 7, the downward pivoting action of the blade 34 is accomplished during an upward stroke of the actuating rod 32. In particular, a distal end 36 of the actuating rod 32 is recessed to form two identical arms bridged by a pin 38, which serves as a fulcrum for the blade 34 a portion of which is rotatably mounted on the pin 38 between these arms. To realize the pivoting motion of the blade 34, the distal end of the body 28 is provided with another pin 42 bridging the bottom of the recess 30 and spaced from the pin 38 such that the blade 34 extends at a right angle to the body 28 in its cutting position. The blade 34 has a short slot 40 providing a cam surface for the pin 42 which traverses the slot 40. In action, when the push rod 32 is pulled up, the blade initially moves linearly upwards because the pin 38 couples the blade 34 and the actuating rod 32. Linear displacement of the blade translates into rotational motion when the pin 42 begins to press against the surface of the slot 40 to generate a torque as the blade 34 attached to the distal end 36 of the connecting rod 32 still moves linearly upwards. A combination of the linear force generated by the rod 32 and the torque created by the pin 42 provides the blade 34 with pivotal motion terminating when the blade 34 extends horizontally into the slit 82 of the adjacent outer dilator 80 in the blade's cutting position. In accordance with one configuration of the blade 34, its opposite edges are both cutting edges capable of providing a cut in opposite directions of the blade's displacement. The actuating rod 32 is eccentrically placed with respect to the axis of symmetry of the body 28 to allow the blade to be fully accommodated within the body 28 in the rest position of the blade.

In accordance with another embodiment of the tissue-cutting instrument 26, the blade 34 pivots to its cutting position during a downward stroke of the actuating rod 32. The blade 34 has the slot 40, as shown in phantom lines in FIG. 7, which is defined between two edges and extends unparallel to the longitudinal axis of the actuating rod 32 in the rest position of the blade. The distal end of the actuating rod 32 is split into two arms attached to one another so that a pin connecting the arms extends through the slot. Accordingly, during a downstroke of the rod 32, its distal end first slides along the slot without affecting its motion, but once the planes in which the rod 32 moves and the slot extends converge, the blade starts rotating about the pin 38 in its cutting position. This structure is principally similar to the above-described structure, but is more effective because the main cut of tissue is made in response to a linear force directed downwards and does not require that the rod 32 be eccentrically placed. To ensure that the tract between the screw heads 60 is properly formed, the tissue-cutting instrument 26 can be installed in the adjacent outer dilator 80, and the entire procedure can be repeated. While the tissue-cutting instrument 26 is shown to have a mechanical structure, any of thermal-, laser-, and ultrasound-cutting instruments can be utilized as well.

Following the formation of the tract, the connecting rod 66 is attached to the screw head 60 of one of the screws 54 by means of a rod holder system 100, as illustrated in FIGS. 8, 9. The rod holder system 100 includes a sleeve 104 slidingly guided through the outer dilator 80 to assume an aligned position, in which a recess 102, formed on the sleeve 104, coincides with the slit 82 provided on the outer dilator 80. In this aligned position, and only in this position, the rod 66 can be displaced to its final position interlinking adjacent screws 54. To ensure such an aligned position between the recess 102 and the slit 82, the opposing surfaces of the sleeve 104 and the outer dilator 80 may be formed with the mating guiding surfaces 93, as explained in reference to FIG. 6. Of course, it is possible to rotate the sleeve 104 relative to the outer dilator manually, if no guiding surfaces are provided.

The criticality of the rod holder 100 is 1) to couple the leading end 70 with the screw head 60, if the screw 54 is configured to have separate parts, and 2) to initiate displacement of the rod 66 in a desired direction so it will bridge the adjacent screw heads. Engagement between the rod 66 and the screw head 60 is realized by releasably locking the trailing end 72 of the rod 66 in the rod holder 100. Numerous holding systems, such as a chuck, a spring-loaded ball mechanism, or simply an O-ring made from frictional material and provided on the inner surface of the sleeve, can be incorporated within the sleeve 104. In case of the spring-loaded ball mechanism, as shown in FIGS. 8–9, balls 108, 110 holding the trailing end 72 of the rod 66 can retract laterally and let the rod 66 go in response to an external force created by the surgeon. Similarly, the O-ring is configured to hold the rod 66 until the external force is applied. If the chuck is provided, the rod holder 100 would have a rotational actuator bringing engaging surfaces of the chuck towards and away from one another. The screw head 60 (FIG. 3) is preliminary rotated in a position in which the pin 68 of the rod 66 automatically extends through and engages the recesses 64 formed in the screw head 60. Alternatively, the inner surface of the outer dilator may be provided with additional guide formations allowing the screw head 60 to slide through the outer dilator 80 only in one position, in which the slots 62 are automatically aligned with the dilator's slit 82. Such a structure can be advantageous for the screw configuration having the leading end 70 of the rod 66 permanently attached to the screw head 60.

Generation of the linearly directed external force, by itself, is not sufficient to pivot the rod 66 between its first and final positions. It is necessary that a torque be applied to the trailing end 72 of the rod 66 causing the latter to pivot about its leading end 70. A structure converting a thrust produced by a push rod 116 into the rotation of the rod 66 includes the specifically configured trailing end 72 of the rod 66 and a distal end of the push rod 116 opposing one another within the rod holder 100. Particularly, as shown in FIG. 9, these ends are complementary slanted to allow the push rod 116 to apply the necessary torque in a desired direction towards the adjacent outer dilator. Thus, once the leading end 70 is coupled to the screw head 60, the push rod 116 is actuated to apply the torque to the trailing end 72 of the rod 66 causing the latter to rotate about is leading end 70 towards the rod's final position.

Figures 10, 11:
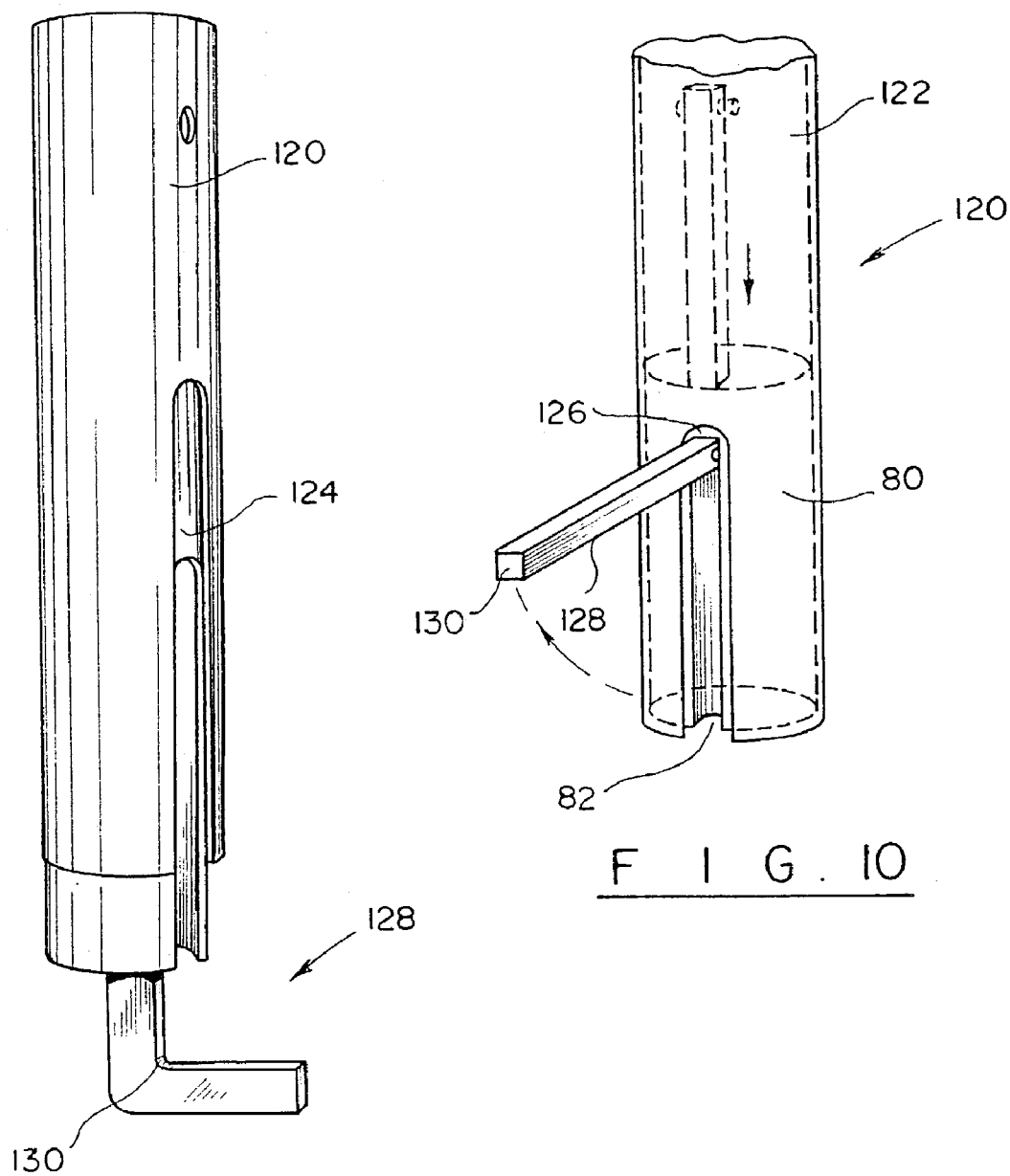
FIG. 10 is an isometric view of one embodiment of the rod holder system configured to establish the final position of the connecting rod, in which the trailing end thereof is received in the second screw.
FIG. 11 is an isometric view of another embodiment of the rod holder system.
Figure 12:
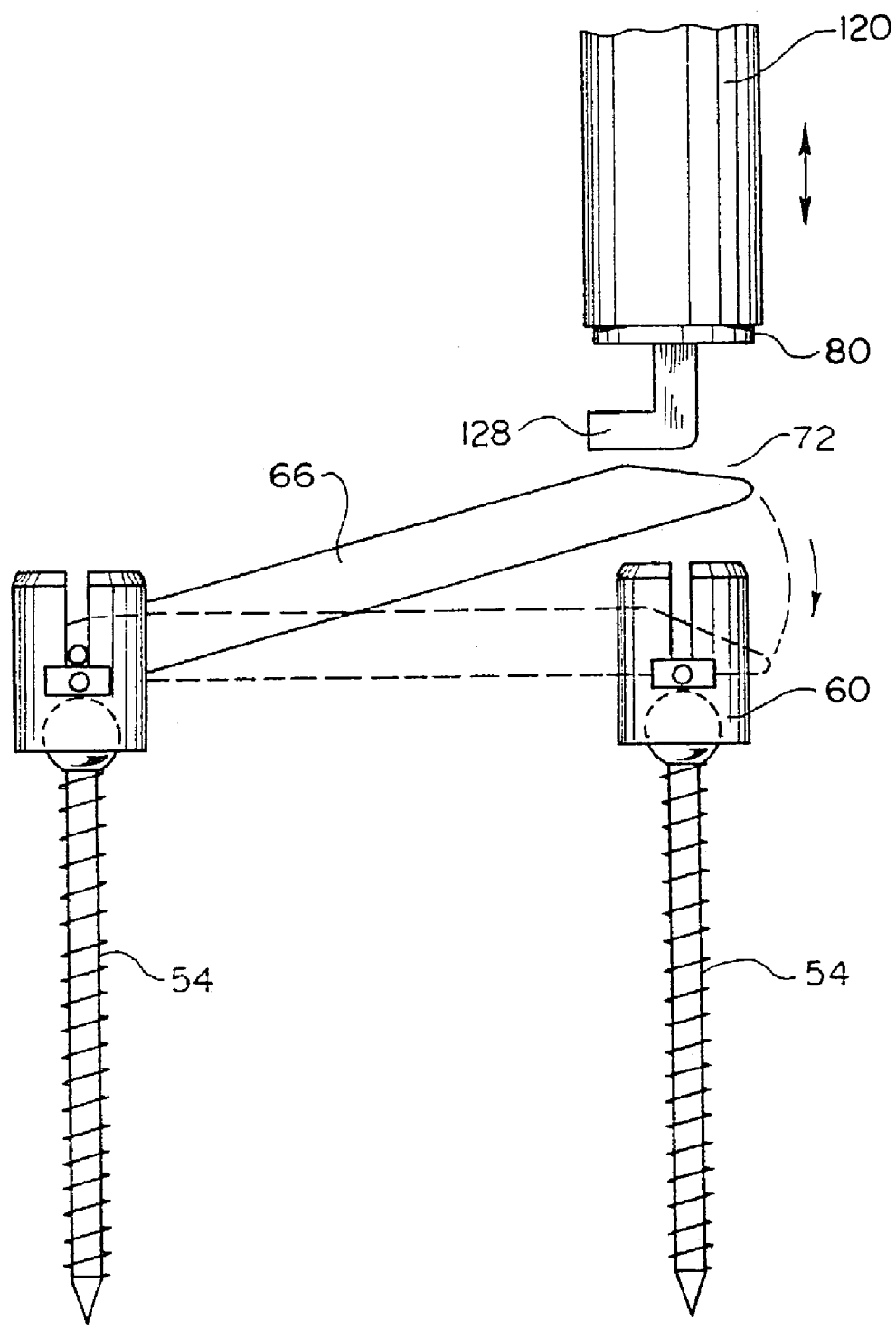
FIG. 12 is a side view illustrating a rod guide system establishing the final position of the connecting rod.

Sometimes the torque applied to the connecting rod 66 may be insufficient to displace the rod 66 all the way to the screw head of the adjacent screw 54. Also, the tract formed between the adjacent screws 54 may not be perfectly shaped and dimensioned to fully accommodate the rod 66. To ensure that the rod 66 assumes its final position, in which the rod is fully received in the tract and the trailing end 72 is lodged in the screw head 60 of the adjacent screw 54, the invention provides for a rod-guiding tool 120 illustrated in FIGS. 10–12. A critical feature of the rod-guiding tool 120 includes an arm 128 capable of engaging and guiding the trailing end 72 of the rod 66 into a respective screw head 60 of the screw 54. One of the inventive embodiments of this tool, as shown in FIG. 10, includes a housing 122 provided with the arm 128 which is spring-loaded to move between a rest position and a deployed position. The arm 128 assumes the deployed position thereof, in which the arm 128 extends generally parallel to the rod receiving tract, when, during downward displacement of the housing 122 through the dilator 80, the arm 128 is fully aligned with the slit 82 of the latter. A free end 130 of the arm can have a paddle-like shape (not shown) configured to press against the trailing end 72 of the connecting rod 66 and to bring it into the screw head 60, as the housing 122 is being pulled upwards. Like the rest of instruments guidable through the outer dilator 80, the housing 122 may have the guiding surface mating with the guiding surface of the outer dilator 80 to establish the alignment between the arm 128 and the slit 82 of the dilator 80.

Still another embodiment of the rod guiding tool 120, as shown in FIG. 11, may have the housing 120 provided with an arm carrier 124 which is formed as a unitary piece having an L-shaped distal end 130 functioning as the arm 128. Displacing the arm carrier 124 downwards within the housing 122 provides actuation of the arm 128.

The above disclosed inventive method and system are directed to interlinking at least a pair of pedicles of the vertebra to be fused identified by placing appropriate landmarks on the skin such that they are aligned with the entry points to the pedicles. An identifying procedure of the inventive process uses an X-ray imaging, fluoroscopic, ultrasound and computer-guiding techniques for identifying the pedicles to be landmarked. In particular, this procedure involves preparing a sterile, transparent sheet of plastic which has on it an outline of the profile of the lumbar spine as seen, for example, from the anteroposterior projection, (hereinafter referred to the A-P) of an image of the spine. Also on this sheet is an oval, for identifying the pedicle from an approximately 30-degree A-P oblique view. These outlines are thin lines incorporated within the substance of the transparent sheet and made of a radioopaque substance, as well as appearing dark to the naked eye so that they are easily recognized lying against the patient's skin. The edges of the transparent sheet has sterile adhesive, which can be exposed and secured once an adequate position is accomplished.

The above disclosed inventive method and system are directed to interlink at least a pair of pedicles of the vertebra to be fused identified by placing appropriate landmarks on the skin such that they are aligned with the entry points to the pedicles. An identifying procedure of the inventive process uses an X-ray imaging, fluoroscopic, ultrasound and computer-guiding techniques for identifying the pedicles to be landmarked. In particular, this procedure involves preparing a sterile, transparent sheet of plastic which has on it an outline of the profile of the lumbar spine as seen, for The sterile sheet with the fiducial incorporated within is placed on the skin of the patient's lumbar spine, and A-P views are obtained. The sheet can be moved until the profile, as seen on the A-P view, is matched with the lateral aspect of the lumbar spine. Appropriate software can be written so that in this way, the various image-guided systems could be utilized if available, but the recommendation would be to still utilize radiological imagery to some degree.

The fiducial sheet is further displaced on the skin so that when the profile of the lumbar spine matches the outlines on the fiducial, an imaging component, such as a fluoroscopic camera, can be brought into an approximately 30-degree A-P oblique view. It has been proposed that this is the most accurate view for viewing the pedicle. This system can be refined further through several adjustments, including a simple system for measuring the angle of the pedicles on pre-op studies. This consists of a compass-like transparency to be placed against the preoperative transaxial images, measuring the angle of the pedicles as they enter the vertebral body. In general, it has been accepted that this angle is approximately 5-degrees at L3, 10-degrees at L4, 15-degrees at L5, and 20-degrees at S1. Given those approximations, which again are generally accepted, most surgeons would accept a fiducial, which arranges the ovals so that when the 30-degree A-P view is utilized, this set of projections of the angles would be identified. However, freestanding ovals with adhesive on one side could also be available if a particular pedicle demonstrated an unusual angle. Utilization of the imaging techniques including X-ray, fluoroscopic, computer-guided and ultrasound imaging techniques requires that instruments of the inventive system, as illustrated in FIGS. 3–24, be radiolucent so as to not block the view of the subcutaneous structures. However, to properly position dilators 80, 86, awls 87, screw 54 and other necessary instruments with respect to the pedicles to be interlinked, it is necessary that their tips located in the vicinity of the pedicles can easily be identified on fluoroscopic views. For example, the importance of the tip of the dilator 80, and only the tip, being metal is reflected in the ease with which this tip can be seen on imaging while dissecting through the tissues which lie between skin and the entry into the pedicle. It is envisioned to outfit the instruments to be imaged with identification reflectors or other instrumentation so that they can be used in association with any of the "Image Guided" systems which are currently available.

Figure 13:
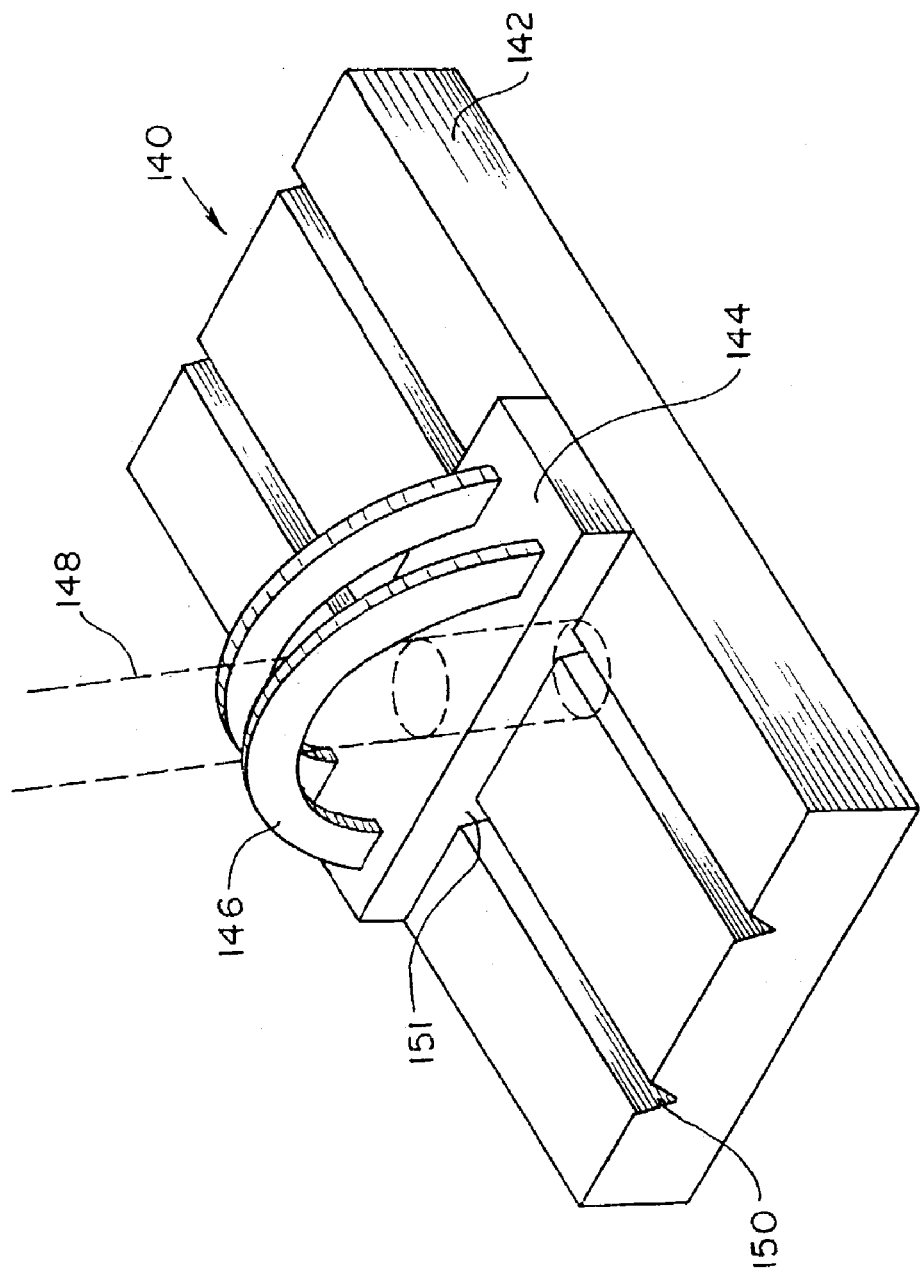
FIG. 13 is an isometric view of a placement system for establishing the desired trajectory of the guide system relative to the entry points into the pedicles to be interlinked.

Identification of landmarks allows the surgeon to utilize a "Free Hand" approach in which an incision, based on the site identified by the landmark, is made in the skin overlying the entry point to the pedicle, and dilators are introduced through the incision. Sometimes, however, such a manual insertion of the dilators may not be sufficient to correctly advance the instruments associated with the screws 54 since the trajectory selected by the surgeon may not be optimal. To overcome this drawback, the inventive system further includes a positioning system or assembly shown in FIGS. 13-23 assisting the surgeon in establishing the desired trajectory of tissue dissecting instruments. As is illustrated in FIG. 13, a placement system 140 enables a hollow guide 148, subsequently traversed by one of the dilators or the sheath 81, to be aligned with the landmark and positioned at a desired angle with respect to the pedicle. Accordingly, the instrument(s) passes through the interior of the hollow guide 148 towards the pedicles along the optimally established screw pathway.

As illustrated in FIGS. 13 and 15, the placement system 140 includes a rectangular outer frame 142, provided with tracks 150, which extend along the spine, an inner frame 144, displaceable along the tracks, and a cradle 146 carrying the guide 148 operative to move transversely to the spine. In accordance with one configuration of the outer frame 142, it has a transparent base, the bottom of which is temporarily attached to the transparent sheet with the landmarks either by adhesive, or by small piercing blades or pins that are inserted into the outer layer of the skin. In accordance with another configuration, as shown in FIG. 16, the outer frame 142 is mounted on two connector stand-holders 152 that connect to the sides of the operating table and operative to establish the desired height of the placement system 140. The outer frame 142 may be locked in a desired position by activating a locking mechanism 154. As an alternative to a centrally recessed one-piece outer base, the outer frame may have a two-half base 156, each provided with a respective track 150. Provision of the two-part base of the outer frame 142 eliminates the necessity of forming a central recess accommodating the guide 148 within the base 156.

The inner frame 144 of the placement system 140 allows the adjustment of the hollow guide 148 along the spine as it slides along the tracks 150 of the outer frame 142. The bottom of the inner frame 144 has guide surfaces 151 (FIGS. 3, 13, 22) extending complementary to the tracks 150 of the outer frame 142 and configured to allow sliding motion of these frames relative to one another. Various cross-sections of the tracks 150 having one of T-, U-, V-, C- and L-shapes necessitating complementary surfaces on the inner frame 144 can be implemented. For example, as shown in FIG. 17, the track 150 is provided with an inverted T-shape having a trapezoidal bottom. FIG. 18 shows a T-shaped recess provided with two undercuts 152, which are formed in upper sides 165 of the track 150. The track 150, as shown in FIG. 19, has an inverted T shape, whereas the bottom of the track 150 of FIG. 20 is provided with a C-shape. FIG. 21 illustrates the track 150 with two lateral surfaces 160 extending inwards from opposite walls of the track 150 and terminating at a distance from one another to form a two-level rectangular compartments 162.

Figure 23:
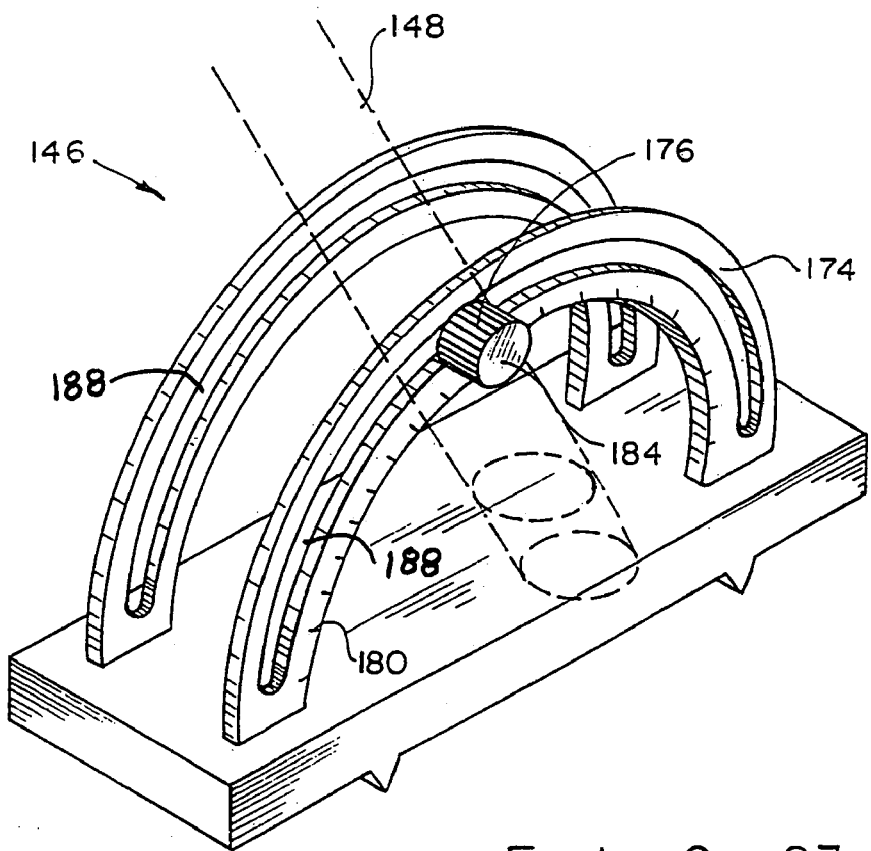
FIG. 23 is another embodiment of the cradle of the placement system of FIG. 13.
Figure 22:
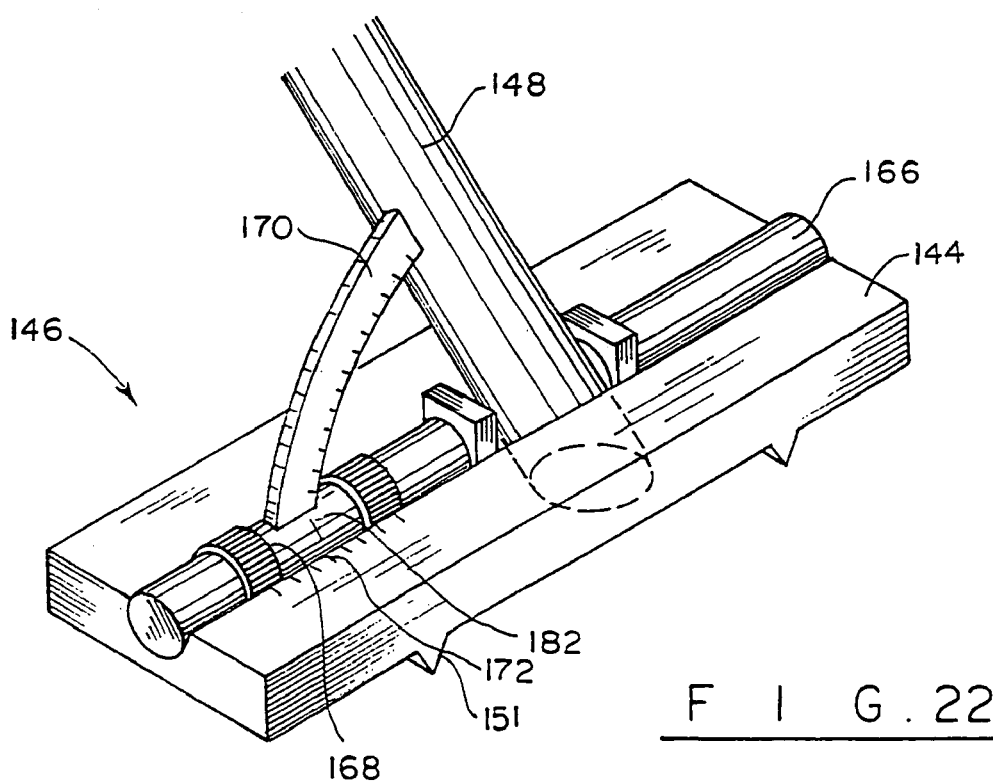
FIG. 22 is an isometric view of one embodiment of the cradle of the placement system illustrated in FIG. 13.

Finally, two modifications of the cradle 146 mounted on the inner frame 144 and providing controllable displacement of the hollow guide 148 in a direction transverse to the longitudinal dimension of the spine is shown in FIGS. 15, 22 and 23. In general, as illustrated in FIG. 15, the inner frame 144 may receive a base of the cradle 146 which, in combination with the outer frame 142, not shown on this figure, provide displacement of the guide 148 in a medial-lateral plane and a cranial-caudal plane. Turning to FIG. 22, the inner frame 144 is provided with a guide rail 166 that can have a polygonal or circular cross-section and has a slide 168 operative to move along the guide rail 166. To angularly displace the guide 148, the slide 168 is provided with an arcuate element 170 rigidly attached to the hollow guide 148, which, in turn, is pivotally mounted on the inner frame 144. A desired angle of the hollow guide 148, derived from preoperative studies by evaluating the angle the pedicle unites with the vertebral body, can be established when a mark 182 on the slide 168 coincides with the desired calibration mark on a scale 172.

The other configuration of the cradle 146, as illustrated in FIG. 23, has a pair of arcuate elements 174 provided with recesses 188, which define a path for the guide 148 mounted on a crossbar 186 slidable along the recesses 188, which are aligned with one another. The crossbar has at least one locking nut 176 provided with a mark 184 that, when brought in alignment with a respective mark on the scale 180 corresponding to the selected angle, indicates the desired angular position of the guide 148, which is then locked in this position by tightening the nut 176 against the guide 174. As a result of the placement system 140, the hollow guide 148 establishes the trajectory of the entry into the pedicle and, in particular, into the oval fiducial demarcating the entry point into the pedicle. The established trajectory allows the screws 54 to pass through the pedicles in the safest way, minimizing risk to important peri-pedicular structures, particularly the nerve roots and thecal sac. Furthermore, the placement system 140 also insures that the screws 54 lie entirely within the pedicle, thus reducing the opportunity for screw breakage or pullout.

For instance, in some embodiments there may be a spinal surgical kit, comprising: a plurality of screws each configured to be percutaneously placed into a respective one of at least two pedicles to be interlinked; and at least one connecting rod having a leading end thereof coupled with a first screw so that the connecting rod pivots between a primary position, in which the connecting rod is aligned with the first screw, to a final position, wherein the connecting rod bridges the first screw and a second screw.

Furthermore, there may be the kit as described above, wherein the first and second screws each have a stem widening from a distal tip to a proximal top thereof and provided with an external thread configured to have a pitch maintaining bone purchase, each of the screws being configured to be passed into a respective pedicle without complete tapping or drilling of the respective pedicle.

Furthermore, there may be the kit as described above, wherein the first and second screws each has a screw head and a rotating component located between and coupled to the top of the stem and the screw head and operative to provide relative rotational motion between the stem and the screw head, which is configured to receive the leading end of the connecting rod.

Furthermore, there may be the kit as described above, wherein the leading end of the connecting rod is permanently coupled to the screw head of the first screw.

Furthermore, there may be the kit as described above, wherein the screw head of the first screw has a pair of aligned recesses detachably receiving a pin provided on the leading end of the connecting rod and configured to provide rotational motion between the connecting rod and the screw head of the first screw.

Furthermore, there may be the kit as described above, wherein the connecting rod is either straight or curved, whereas the screw heads of the first and second screws are rotatably adjustable relative to one another upon placing the screws in the pedicles to receive the leading and trailing ends of the connecting rod.

Furthermore, there may be the kit as described above, wherein the rotating component includes a joint ball assembly having a ball formed on the top of the stem of each screw and a socket receiving the ball formed in a bottom of the screw head.

The above description should not be construed as limiting, but merely as exemplification of preferred embodiments. For example, a combination of the above-disclosed instruments can constitute a spinal surgical kit. Those skilled in the art will envision other modifications within the scope and spirit of the present disclosure as defined in the following appended claims.

What is claimed is:

1. A method of stabilizing the spine of a patient, comprising the steps of:
    identifying and marking landmarks each corresponding to an entry point to respective pedicles of at least two vertebra of the spine;
    guiding screws each through a respective entry point into the respective pedicles of the at least two vertebra;
    guiding a pin, provided on a leading end of a connecting rod and extending perpendicular to a longitudinal axis thereof, through a pair of aligned recesses formed in a screw head of a first screw to mount the connecting rod on the first screw;
    coupling the leading end of the connecting rod to the first screw head with the pin in a first position of the connecting rod, in which the connecting rod is aligned with the first screw; and
    displacing the connecting rod about the pin at the leading end thereof so that a trailing end of the connecting rod engages a second screw of a second vertebrae in a final position of the connecting rod.

2. The method of claim 1, wherein the screws each are percutaneously placed into the pedicles of the first and second vertebra on a same side of the length of the spine.

3. A spinal surgical kit, comprising:
    a plurality of screws, each configured to be percutaneously placed into a respective one of at least two pedicles to be interlinked; and
    at least one connecting rod having a longitudinal axis, a leading end, and a pin positioned proximal to the leading end, the leading end coupled with a first screw so that the connecting rod is able to pivot about a longitudinal axis of the pin between a first position, in which the connecting rod is generally parallel to a longitudinal axis of the first screw, and a final position, in which the connecting rod is generally transverse to the longitudinal axis of the first screw such that the connecting rod bridges the first screw and a second screw,
    wherein a first screw head has a pair of opposed recesses such that the pin when seated in the recesses rotatably mounts the connecting rod to the first screw head.

4. The spinal surgical kit of claim 3, wherein the first and second screws each has a stem widening from a distal tip to a proximal top thereof and provided with an external thread configured to have a pitch maintaining bone purchase, each of the screws being configured to be passed into a respective pedicle without complete tapping or drilling of the respective pedicle.

5. The spinal surgical kit of claim 3, wherein the first and second screws each has a screw head and a rotating component located between and coupled to the top of the stem and the screw head and operative to provide relative rotational motion between the stem and the screw head.

6. The spinal surgical kit of claim 5, wherein the rotating component includes a joint ball assembly having a ball formed on the top of the stem of each screw and a socket receiving the ball formed in a bottom of the screw head of each screw.

7. The spinal surgical kit of claim 3, wherein the connecting rod has one of a straight or curved shape, and the screw heads of the first and second screws are rotatably adjustable relative to one another upon placing the screws in the pedicles to receive the leading and trailing ends of the connecting rod.

8. A medical system comprising:
    first and second pedicle screws, each screw having a screw head rotatably coupled thereto, each screw head having at least one slot, and the first screw head having a pair of aligned recesses spaced uniformly from the at least one slot; and
    a connecting rod, having a longitudinal axis, the connecting rod coupled to a pin which is located in proximity to a leading end of the connecting rod, wherein the pin is seated in the pair of recesses so that the connecting rod is rotatably mounted to the first screw head thereby enabling the connecting rod to pivot about a longitudinal axis of the pin to engage the at least one slot of the second screw head.

9. The spinal surgical kit of claim 8, wherein the leading end of the connecting rod is detachably coupled to the screw head of the first screw.

10. A spinal surgical kit, comprising:
a plurality of screws each configured to be placed into a respective one of at least two pedicles to be interlinked; wherein a first screw of the plurality of screws has a screw head having a pair of opposed recesses;
at least one connecting rod having a leading end and a pin positioned proximal to the leading end, wherein the pin is seated in the opposed recesses so that the connecting rod is rotatably mounted to the first screw head such that the connecting rod is able to pivot about a longitudinal axis of the pin between a first position, in which the connecting rod is generally parallel to a longitudinal axis of the first screw, and a final position, in which the connecting rod is generally transverse to the longitudinal axis of the first screw such that the connecting rod bridges the first screw and a second screw.

11. The spinal surgical kit of claim 10, wherein the connecting rod has one of a straight or a curved shape, and the screw heads of the first and second screws are rotatably adjustable relative to one another upon placing the screws in the pedicles to receive the leading and trailing ends of the connecting rod.

12. The spinal surgical kit of claim 10, further comprising a joint ball assembly on each screw, the joint ball assembly having a ball formed on the top of the stem of each screw and a socket receiving the ball formed in a bottom of the screw head of each screw.

13. The spinal surgical kit of claim 10, wherein the leading end of the connecting rod is detachably coupled to the screw head of the first screw.

14. A medical system comprising:
first and second pedicle screws, each screw having a screw head coupled thereto,
a pin formed as an integral part of the first screw head,
a connecting rod having a longitudinal axis, the connecting rod permanently coupled to the pin so that the connecting rod is rotatably coupled to the first screw head, thereby enabling the connecting rod to pivot about a longitudinal axis of the pin between a first position wherein the longitudinal axis of the connecting rod is generally parallel to a longitudinal axis of the first screw and a second position wherein the longitudinal axis of the connecting rod is generally transverse to the longitudinal axis of the first screw such the connecting rod bridges the first screw and the second screw.

* * * * *

UNITED STATES PATENT AND TRADEMARK OFFICE
CERTIFICATE OF CORRECTION

PATENT NO. : 7,306,603 B2 Page 1 of 1
APPLICATION NO. : 10/320989
DATED : December 11, 2007
INVENTOR(S) : Frank Boehm, Jr. and Benedetta D. Melnick It is certified that error appears in the above-identified patent and that said Letters Patent is hereby corrected as shown below:

Title page, the following passage is currently listed as:

(75)  Inventors:  Frank H. Boehm, Jr., Utica, NY (US);
                  Benedetta D. Meinick, Rome, NY (US)

This should be changed to:

(75)  Inventors:  Frank H. Boehm, Jr., Utica, NY (US);
                  Benedetta D. Melnick, Rome, NY (US)

Signed and Sealed this

Twenty-seventh Day of May, 2008

JON W. DUDAS
*Director of the United States Patent and Trademark Office*